US012806327B2

(12) United States Patent
Folan et al.

(10) Patent No.: US 12,806,327 B2
(45) Date of Patent: Nov. 24, 2026

(54) SYSTEM FOR WOUND THERAPY

(71) Applicant: Boston Scientific Scimed, Inc., Maple Grove, MN (US)

(72) Inventors: Martyn G. Folan, Galway (IE); Jonathan Root, Townsend, MA (US); Emma Horgan, Galway (IE); Gary Gilmartin, Foxford (IE); Michael Walsh, Corofin (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 640 days.

(21) Appl. No.: 18/316,595

(22) Filed: May 12, 2023

(65) Prior Publication Data

US 2023/0372602 A1 Nov. 23, 2023

Related U.S. Application Data

(60) Provisional application No. 63/364,934, filed on May 18, 2022.

(51) Int. Cl.
*A61M 1/00* (2006.01)
*A61B 17/11* (2006.01)

(52) U.S. Cl.
CPC ........... *A61M 1/90* (2021.05); *A61B 17/1114* (2013.01)

(58) Field of Classification Search
CPC ..... A61M 1/90; A61M 1/915; A61B 17/1114; A61B 2017/00637; A61B 17/0057; A61B 2017/00654; A61F 13/05
See application file for complete search history.

(56) References Cited

U.S. PATENT DOCUMENTS

| | | | | |
|---|---|---|---|---|
| 7,691,153 | B2 | 4/2010 | Benz et al. | |
| 9,179,921 | B1 | 11/2015 | Morris | |
| 10,058,413 | B2 | 8/2018 | Heiss | |
| 10,722,622 | B2 | 7/2020 | Loske | |
| 2002/0107541 | A1* | 8/2002 | Vale | A61F 2/0108 606/200 |
| 2013/0110066 | A1* | 5/2013 | Sharma | A61L 31/04 514/772.3 |
| 2014/0031773 | A1* | 1/2014 | Mikkaichi | A61M 3/0279 604/319 |
| 2015/0148785 | A1 | 5/2015 | Kleiner | |
| 2019/0262182 | A1* | 8/2019 | Collinson | A61F 13/05 |

(Continued)

OTHER PUBLICATIONS

International Search Report and Written Opinion in PCT/US2023/022030, mailed Jul. 26, 2023 (6 pages).

(Continued)

*Primary Examiner* — Philip R Wiest
*Assistant Examiner* — Peter Daniel Smith
(74) *Attorney, Agent, or Firm* — Bookoff McAndrews, PLLC

(57) ABSTRACT

A medical device, comprising a tube having a sidewall defining a lumen within the tube, wherein a plurality of openings extend through a distal portion of the sidewall and are in fluid communication with the lumen; a support structure coupled to the distal portion of the sidewall, the support structure having a contracted configuration and an expanded configuration, and the support structure having support openings through a wall of the support structure; and a porous body over at least a portion of the support structure.

13 Claims, 7 Drawing Sheets

(56) References Cited

U.S. PATENT DOCUMENTS

| | | | | |
|---|---|---|---|---|
| 2020/0016301 | A1 | 1/2020 | Kleiner | |
| 2020/0276056 | A1* | 9/2020 | Leeds | A61F 13/05 |
| 2021/0260335 | A1* | 8/2021 | Burke | A61M 25/0023 |
| 2021/0267813 | A1* | 9/2021 | Wales | A61F 13/266 |
| 2022/0022854 | A1* | 1/2022 | Lashinski | A61B 17/0057 |
| 2022/0370255 | A1* | 11/2022 | Locke | A61F 13/05 |

OTHER PUBLICATIONS

"Endo-Sponge®." Global—B. Braun Melsungen AG, https://www.bbraun.com/en/products-and-solutions/therapies/sutures-and-surgical-specialties/endoluminal-vacuum-therapy/endo-sponge-endoluminal-vacuum-therapy.html.

"VAC-Stent Registry—Full Text View." Full Text View—ClinicalTrials.gov, https://clinicaltrials.gov/ct2/show/NCT04884334.

https://vac-stent.com.

Leeds, M., et al. (2016)—Endoluminal Vacuum Therapy for Esophageal and Upper Intestinal Anastomotic Leaks—JAMA Surgery.

Bludau, M., et al. (2018)—Results of endoscopic vacuum-assisted closure device for treatment of upper GI leaks—Surgical Endoscopy (2018) 32:1906-1914.

Chon S. et al., (2020)—VACStent: a new option for endoscopic vacuum therapy in patients with esophageal anastomotic leaks after upper gastrointestinal surgery—Endoscopy. May 2020;52(5):E166-E167.

* cited by examiner

SYSTEM FOR WOUND THERAPY

CROSS-REFERENCE TO RELATED APPLICATIONS

This application claims the benefit of priority under 35 U.S.C. § 119 from U.S. Provisional Application No. 63/364,934, filed May 18, 2022, which is incorporated by reference herein in its entirety.

TECHNICAL FIELD

This disclosure relates generally to medical treatment systems, devices, and related methods thereof. Embodiments of the disclosure relate to endoluminal wound treatment systems, and medical devices for negative pressure wound therapy.

BACKGROUND

Endoscopic and open surgical procedures of the gastrointestinal (GI) tract include, for example, colonic resection, bariatric surgery, esophagectomy, gastric bypass, and sleeve gastrectomy, among others. These procedures may result in perforation, post-surgical leaks, or other wounds of the tract. Limited treatment options exist for managing such wounds, which have significant morbidity and mortality rates. Options include surgical re-operation and endoscopic placement of a stent or clips. Surgery is relatively invasive and also has high morbidity and mortality rates. Endoscopic stent placement is a less invasive option. The placed stent, however, can migrate from the intended location and/or wall off infection at the treatment site, inhibiting drainage.

SUMMARY

Aspects of the disclosure relate to, among other things, systems, devices, and methods for treating a target treatment site using negative pressure with an expandable member, among other aspects. Each of the aspects disclosed herein may include one or more of the features described in connection with any of the other disclosed aspects.

According to an example, a medical device includes a tube having a sidewall defining a lumen within the tube, wherein a plurality of openings extend through a distal portion of the sidewall and are in fluid communication with the lumen. The medical device includes a support structure coupled to the distal portion of the sidewall, the support structure having a contracted configuration and an expanded configuration, and the support structure having support openings through a wall of the support structure. The medical device includes a porous body over at least a portion of the support structure.

Any of the medical devices described herein may include one or more of the following features. The distal portion of the sidewall may extend along an inside of the wall of the support structure. The plurality of openings may be spaced along a distal length of the tube. The tube may be movably coupled to a distal portion of the support structure. In some embodiments, the tube is rotatable about an axis of the tube relative to the support structure and the porous body. The plurality of openings may be circumferentially spaced approximately 180 degrees apart on the sidewall of the tube. The support structure may further comprise an open proximal end through which the tube extends. The support structure, in the expanded configuration may comprise a distal bulbous region, a proximal region and a lip region between the distal bulbous region and the proximal region, wherein a cross sectional dimension of the lip region is smaller than a cross sectional dimension of the bulbous region and a cross sectional dimension of the proximal region. The porous body may be a flexible sponge. The porous body may surround at least a portion of a circumference of the support structure. The porous body may be affixed to the support structure. The porous body may further comprise multiple stacked layers of porous material capable of being individually removed through a distal opening in the support structure and an interior of the support structure. The porous body may further comprise strips of material extending from a distal end to a proximal end of the support structure. The medical device may further comprise a tear line between adjacent stacked layers. In some embodiments, at least one of the stacked layers may be removable through the distal opening by pulling a pull line.

According to another example, a medical device comprises a sheath, a tube having a sidewall defining a lumen within the tube, wherein a plurality of openings extend through a distal portion of the sidewall and are in fluid communication with the lumen, so that application of suction within the lumen results in suction through the plurality of openings, wherein the tube includes a distal portion having a contracted configuration inside the sheath and an expanded configuration distal to the sheath; and a porous body over at least the distal portion, so that the suction through the support openings results in suction through pores of the porous body.

Any of the medical devices described herein may include one or more of the following features. The distal portion of the tube may be substantially straight in the contracted configuration and at least partly spiraled, spherical, elliptical, pyramidal, or cubical in the expanded configuration. The plurality of openings may be spaced along the distal portion of the tube.

According to another example, for example, a method of applying suction to a tissue, the method may comprise inserting a distal portion of a medical device in an unexpanded state into a cavity, the medical device comprising a tube and the distal portion, wherein the distal portion includes a support structure attached to the tube, and a porous body attached to the support structure; expanding the distal portion such that an external wall of the porous body contacts an internal wall of the cavity; and applying suction to the tissue through a plurality of openings in the tube and pores in the porous body. The method may further comprise removing at least a portion of the porous body from the support structure, without removing a remainder of the distal portion from the cavity.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of this disclosure and together with the description, serve to explain the principles of the disclosure.

DETAILED DESCRIPTION

Figure 1B:
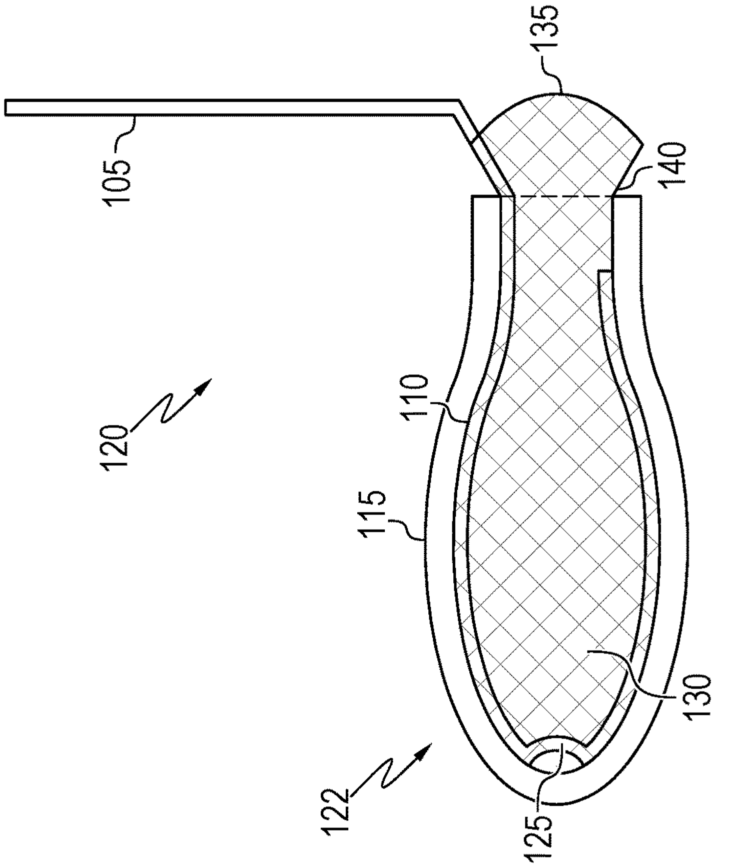
FIGS. 1A and 1B are side views of an exemplary device in an expanded configuration (1A) and in a contracted, or closed, configuration (1B), according to aspects of this disclosure.

Endoluminal vacuum therapy (EVAC) has been proposed. In EVAC, negative pressure is delivered to the wound site in the GI tract, for example through a nasogastric tube having a sponge at its terminal end. The sponge is placed endoscopically into the perforation, leak, or other wound. Negative pressure then is applied. Devices and systems suited for EVAC are limited, however.

Examples of the disclosure include systems, devices, and methods for removing materials from a target site within a subject (e.g., patient) by generating a negative pressure therein. Embodiments of this disclosure include devices, systems, and methods for endoluminal vacuum therapy (EVAC). In examples, EVAC includes endoluminal placement of a porous body, e.g., a sponge or other like material into the wound site, including a perforation, a cyst, a leak, an anastomosis, etc. Placement of the material may be via a catheter, scope (endoscope, bronchoscope, colonoscope, etc.), tube, or sheath, inserted into the GI tract via a natural orifice. The orifice can be, for example, the nose, mouth, or anus, and the placement can be in any portion of the GI tract, including the esophagus, stomach, duodenum, large intestine, or small intestine. Placement also can be in other organs reachable via the GI tract.

Furthermore, in embodiments of this disclosure, the sponge of the EVAC devices may be any suitable biocompatible material that may absorb liquids and/or permit liquid to pass therethrough via negative pressure. For example, negative pressure may be used to draw bodily liquids and/or other materials present at a tissue treatment site through the porous body. The material may be flexible, compressible, porous, hydrophilic, sterile, and/or disposable. The sponge material may be an open-cell foam. Suitable materials include polyurethanes, esters, ethers, composite materials, and any medical-grade material. Furthermore, in some aspects, the sponge may be referred to synonymously as a porous body. Therapeutic additives in the sponge such as, for example, hydrogen peroxide, steroids, and various wound sprays can be utilized to help treat eosinophilic esophagitis and other defects of the esophagus or otherwise aide in the therapy being applied.

Reference will now be made in detail to aspects of this disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the patient. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." Further, relative terms such as, for example, "about," "substantially," "approximately," etc., are used to indicate a possible variation of ±10% in a stated numeric value or range.

Figure 1A:
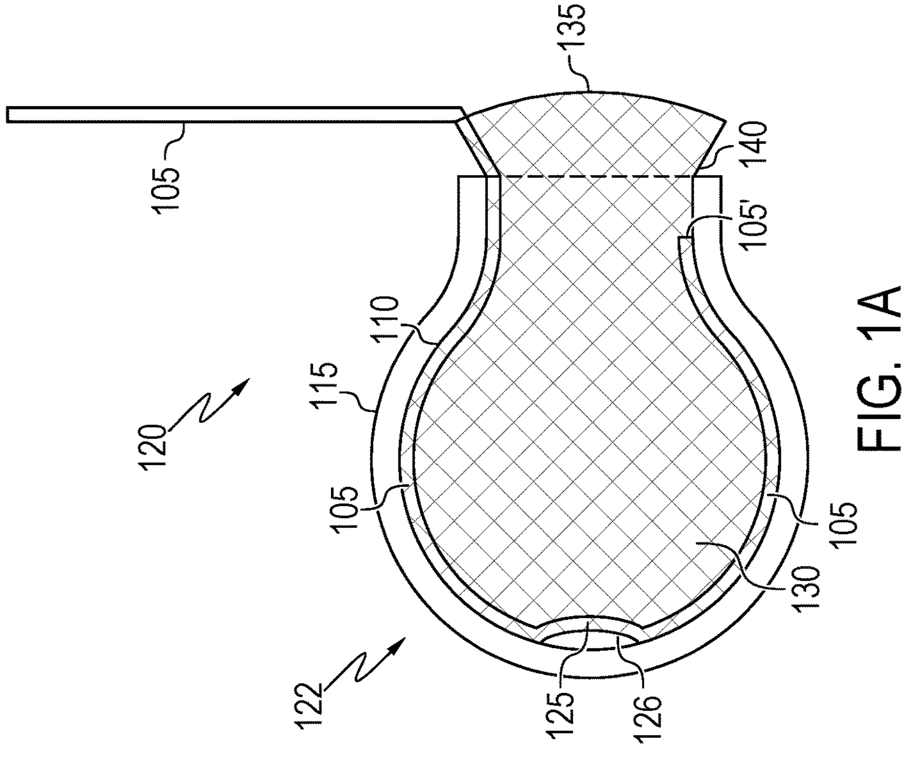

FIGS. 1A and 1B are side views of an exemplary device 120 in an expanded configuration (1A) and in a contracted, or closed, configuration (1B), according to aspects of this disclosure.

Medical device 120 may include a negative pressure conduit 105, which may, for example, include a tube, such as a flexible tube or a nasal tube. Negative pressure conduit 105 may be connected to a vacuum source 107 (shown in FIG. 3), such as a portable or centralized pump or other mechanism for generating negative pressure in conduit 105 and located at a proximal end of a sponge delivery system 100 of FIG. 3 (e.g., near an operator of sponge delivery system 100). The negative pressure may be conveyed through a supply tube or other conveyance mechanism to conduit 105. Referring back to FIGS. 1A and 1B, negative pressure conduit 105 may have one or more openings (not shown) in a distal portion of conduit 105 and in fluid communication with one or more pores (or other types of openings) of a sponge 115, such that a negative pressure from negative pressure conduit 105 may be applied through sponge 115 to surrounding tissue or other patient anatomy. Vacuum source 107 and negative pressure conduit 105 may apply a constant negative pressure or a variable negative pressure, depending on the needs of the medical procedure.

Medical device 120 may include an end effector 122 coupled to the distal end of negative pressure conduit 105. End effector 122 may comprise a hollow expanding frame 110, wherein the expanding frame 110 has support openings through a sidewall of the expanding frame 110. Expanding frame 110 may be comprised of any suitable material capable of collapsing and expanding to any original shape (e.g., nitinol). Furthermore, expanding frame 110 may be capable of allowing suction or negative pressure to pass through the support openings of the sidewalls of expanding frame 110. Expanding frame 110 may include, for example, baskets, meshes, cages, loops, braids, scaffolds, wires, filaments, cables, string, thread, coils, or other support structures which may facilitate transitions between collapsed configurations and expanded configurations. Expanding frame 110 may have shape memory properties and/or may be biased into the expanded configuration. Alternatively or additionally, a secondary medical device (e.g., a balloon) (not shown) may be used to expand the frame to a desired size/diameter.

Referring to end effector 122 in the expanded configuration (FIG. 1A), expanding frame 110 may have a bulbous region 130, wherein the overall diameter or cross-sectional dimension of bulbous region 130 is larger than the overall diameter or cross sectional dimension at a neck region at a proximal end 135 or a tapered region at a distal end 125 of expanding frame 110. Distal end 125 of expanding frame 110 may comprise a terminal opening 126 wherein there is an absence of framing material. Terminal opening 126 may face distally. Alternatively or additionally, distal end 125 may comprise a distalmost point at which the framing material meets and/or terminates. Similarly, proximal end 135 of expanding frame 110 may comprise a proximally-facing opening wherein there is an absence of framing material and/or may comprise a proximalmost point at which the framing material meets and/or terminates. In some embodiments, the terminal opening 126 is sufficiently sized to allow a tube or guide wire to pass through expanding frame 110 from distal end 125 to proximal end 135. Terminal opening 126 may also be suitably sized and shaped for passing secondary devices, such as biopsy devices, injectable contrast, and/or one or more pharmaceutical or cleansing agents. Distal to proximal end 135, expanding frame 110 may comprise a lip 140, or narrowed region, wherein the overall diameter or cross-sectional dimension is smaller as compared to that of both bulbous region 130 and a region of expanding frame 110 at proximal end 135. Lip 140 assists in the placement and retention of the device in a cavity (shown in more detail in FIGS. 2A-2C and to be described in further detail herein), among other things.

As previously described, expanding frame 110 may be braided, knitted, or similarly constructed in a manner comparable or similar to an expandable stent commonly known in the art. Expanding frame 110 may further comprise coatings or additives to aid in the therapeutic application of device 120. For example, expanding frame 110 may be coated partially or completely with or comprised partially or completely of a fluoroscopic material to aid in visualization in certain procedures. Alternatively or additionally, expanding frame 110 may be coated partially or completely with therapeutic agents to aid or assist in the therapy being delivered.

End effector 122 also includes sponge 115, wherein sponge 115 may surround an external-most wall of expanding frame 110. Sponge 115 may be attached to expanding frame 110 by adhesives, a friction fit, or other means commonly known in the art. Lip 140 may also assist in the retention and placement of sponge 115 to expanding frame 110. Sponge 115 may extend over the terminal opening 126. Alternatively, sponge 115 may comprise an opening (not shown) that lies over and communicates with terminal opening 126. Sponge 115 may be any desired thickness around expanding frame 110. For example, one or more dimensions (e.g., length, height/thickness, width, diameter, etc.) of sponge 115 may correspond to a size of a wound. Similarly, sponge 115 may mimic or otherwise replicate the size and shape of expanding frame 110. For example, when expanding frame 110 is in a collapsed state, sponge 115 is also in a collapsed state, as shown in FIG. 1B, due to a fixed connection between sponge 115 and expanding frame 110. In some embodiments, a user may change or alter the desired shape of sponge 115 by cutting, tearing, pressing, or otherwise manipulating sponge 115. The adjustability of sponge 115 may facilitate achieving a desired size of the sponge, as it may be desirable for sponge 115 to have dimensions that substantially correspond to dimensions of a cavity or wound, e.g., a size of an orifice of the wound. Furthermore, as the wound or cavity heals or while the vacuum is on, the size of the wound or cavity may change, and a differently sized sponge 115 may be necessary or desirable.

The negative pressure conduit 105 may extend adjacent to, and contact, an internal wall of expanding frame 110 from proximal end 135 to distal end 125. As shown in FIGS. 1A and 1B, conduit 105 then extends proximally from distal end 125 towards proximal end 135 and terminates at terminal end 105' of conduit 105. Conduit 105 may extend around terminal opening 126 or across terminal opening 126. Conduit 105 may be attached to the expanding frame 110 by adhesives or other means commonly known in the art. Negative pressure conduit 105 may have a plurality of pores (not shown) randomly or incrementally dispersed along a desired length of conduit 105 in the portion of conduit 105 within expanding frame 110. The plurality of pores enable suction at the target wound site. Though one negative pressure conduit 105 is shown in FIGS. 1A and 1B, additional conduits may be utilized to increase suction and/or disperse suction throughout expanding frame 110 and sponge 115. Additionally or alternatively, one or more negative pressure conduits can split, e.g., one conduit splits to two, three, four, etc. conduits within expanding frame 110, much like fingers emanating from a hand/arm. Negative pressure conduit 105 may surround the internal wall of the expanding frame at certain points, like a tube in a stent. Alternatively, a more expansive arrangement may be envisaged, wherein negative pressure conduit 105 surrounds the internal wall of the expanding frame more extensively.

In a closed or compressed configuration (FIG. 1B), the longitudinal length of the end effector 122 may increase while the height or width may decrease as compared to the expanded state of FIG. 1A, similar to a stent. The compressibility of frame 110 may facilitate delivery of medical device 120. For example, medical device 120 may be delivered to a target site in the compressed configuration. The compressed configuration may be small enough that at least portions of the medical device 120 may fit in a working channel of an endoscope or may otherwise be endoscopically delivered. Upon deployment, medical device 120, and specifically end effector 122, may transition to an expanded configuration, in which end effector 122 may engage with tissue of a subject (e.g., a wound).

Figure 2A:
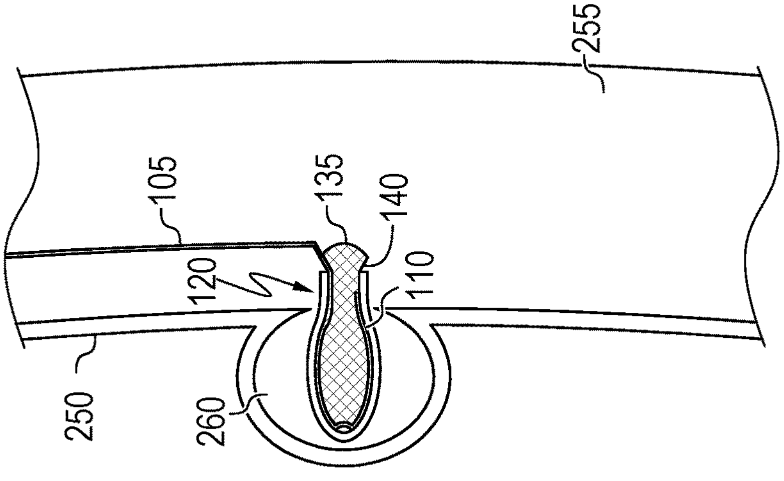
FIGS. 2A, 2B, and 2C illustrate views of the medical device of FIGS. 1A and 1B in an exemplary method of treatment, according to aspects of the disclosure.
Figure 2B:
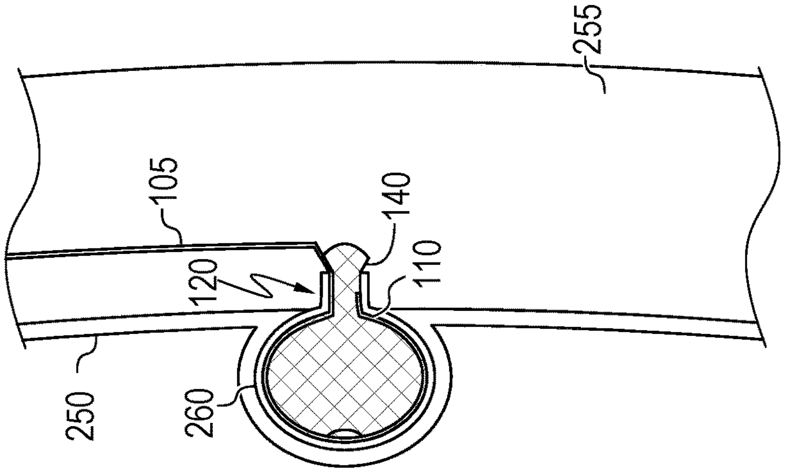
Figure 2C:
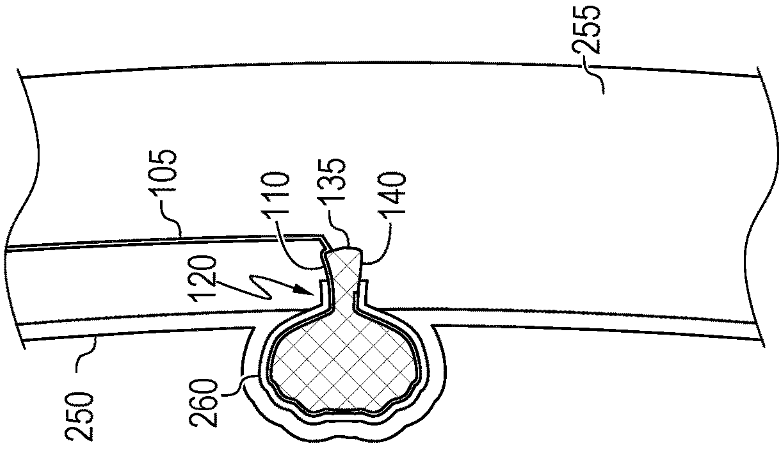

FIGS. 2A-2C depict medical device 120 during different stages of use. More specifically, FIGS. 2A-2C depict an esophageal lumen 255 with a wound, perforation, or cavity 260 in esophageal wall 250. As shown in FIG. 2A, the medical device 120, or at least a distal portion of medical device 120 such as a portion distal to lip 140, is delivered within cavity 260 of the esophageal lumen 255 in an unexpanded state. Medical device 120 may be delivered by advancing device 120 over a guide wire or tube (not shown) or within a lumen of a scope, sheath, or other like device. Once in place, medical device 120 is expanded, as shown in FIG. 2B. Device 120, and specifically end effector 122, may be expanded either by virtue of the material of frame 110 once end effector 122 is deployed out of a sheath, and/or end effector 122 may be expanded by a secondary device, such as a balloon (not shown) expanded inside of frame 110. End effector 122 fills the cavity 260 such that an external wall of sponge 115 contacts an internal wall of the cavity 260. Lip 140 may further assist in keeping end effector 122 in position within cavity 260, by larger diameter portion of end effector 122, adjacent each side of lip 140, sandwiching tissue and/or contacting both sides of tissue, so that end effector 122 does not migrate further into or out of cavity 260.

Once end effector 122 is in place and expanded (as shown in FIG. 2B), the vacuum source is turned on and the internal walls of cavity 260 are drawn in towards sponge 115 by the vacuum, as shown in FIG. 2C. Device 120 is then left in place for a period of time ranging from approximately about less than one day to approximately about seven days or longer. Once cavity 260 is sufficiently reduced in size, sponge 115 and frame 110 are retracted from cavity 260 and a new device 120 having a sponge 115 and frame 110 are rep laced to fill the smaller cavity 260, if desired. The process may then be repeated as many times as necessary with a new device 120.

Figure 3:
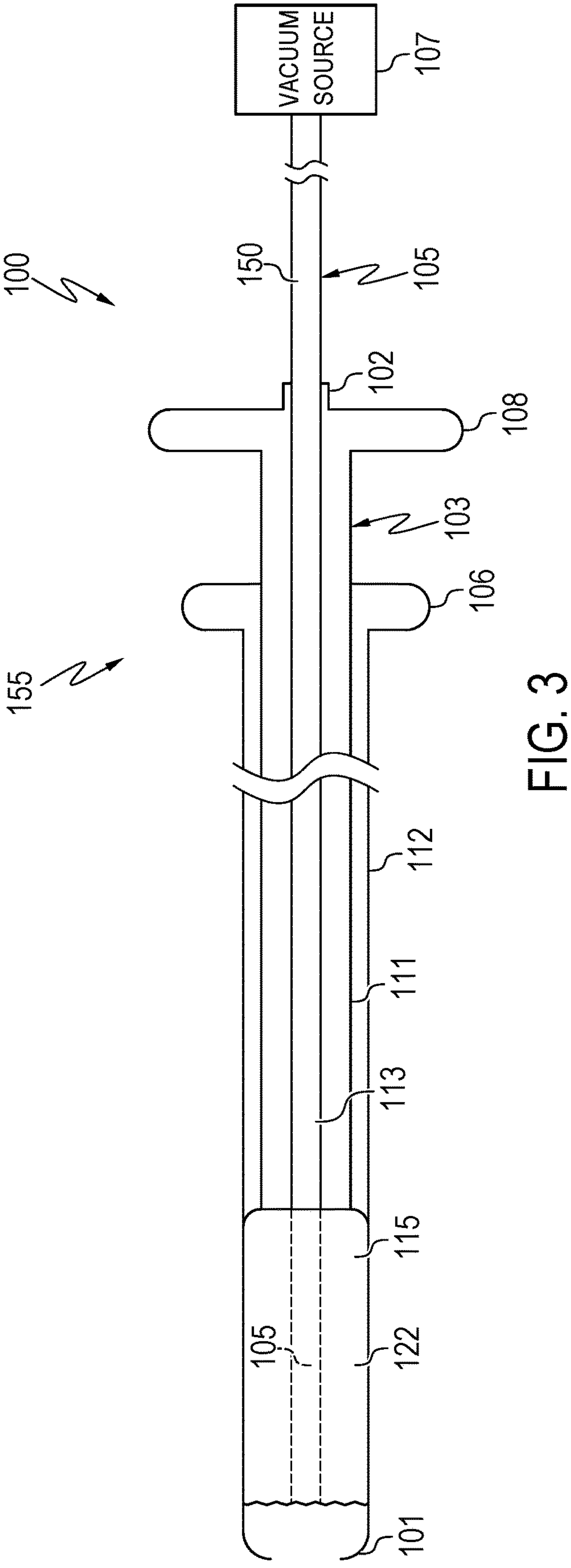
FIG. 3 is a cross-sectional view of an exemplary delivery system, according to aspects of this disclosure.

FIG. 3 is a cross-sectional view of an exemplary delivery system 100 for delivery of device 120. A proximal portion of delivery system 100 may include a handle 155. Handle 155 may include an inner tubular member 103 and an outer tubular member 112. Finger grips 106 may project radially outward from a proximal portion of outer tubular member 112. Similarly, finger grips 108 may project radially outward from a proximal portion of inner tubular member 103. Outer tubular member 112 may include an inner lumen 111 to receive a portion of the inner tubular member 103 and to facilitate axial movement of inner tubular member 103 within outer tubular member 112. Finger grips 106, 108 facilitate a user pushing inner tubular member 103 within lumen 111 of outer tubular member 112 and in an axial direction. An external surface of Inner tubular member 103 and/or an internal surface of outer tubular member 112 may be coated with a lubricious material (e.g., polytetrafluoroethylene, or PTFE) to assist in the movement of inner tubular member 103 within outer tubular member 112.

An inner lumen 113 of inner tubular member 103 may serve as at least a portion of conduit 105 of device 120. End effector 122 may be fixed to a distal end of inner tubular member 103. Lumen 113 may be connected to a tube 150 extending from a proximal end of handle 155, tube 150 and lumen 113 together forming conduit 105. Tube 150 includes a proximal end connected to a vacuum source 107. In an exemplary embodiment, an opening 102 is at a proximal-most portion of inner tubular member 103. Opening 102 may be removably coupled to tube 150 by means, for example, of a luer lock or other removable fitting commonly known in the art. Opening 102 may facilitate fluid flow from vacuum source 107, through lumen 113 of the inner tubular member 112.

Alternatively, tube 150 may extend through opening 102 and through lumen 113 and connect to end effector 122. Tube 150 then would serve as conduit 105. In this embodiment, tube 150 and end effector 122 may move axially relative to lumen 113.

A distal portion of delivery system 100 may include a distal opening 101 disposed at a distal-most end. Opening 101 enables the ejection or release of medical device 120, and specifically its end effector 122, from outer tubular member 112. For example, when the inner tubular member 103 is transitioned from a first proximal configuration to a second distal configuration within outer tubular member 112, end effector 122 may be pushed out of or ejected from the distal opening 101. Ejection from opening 101 permits end effector 122 to transition to its expanded configuration.

Figure 4B:
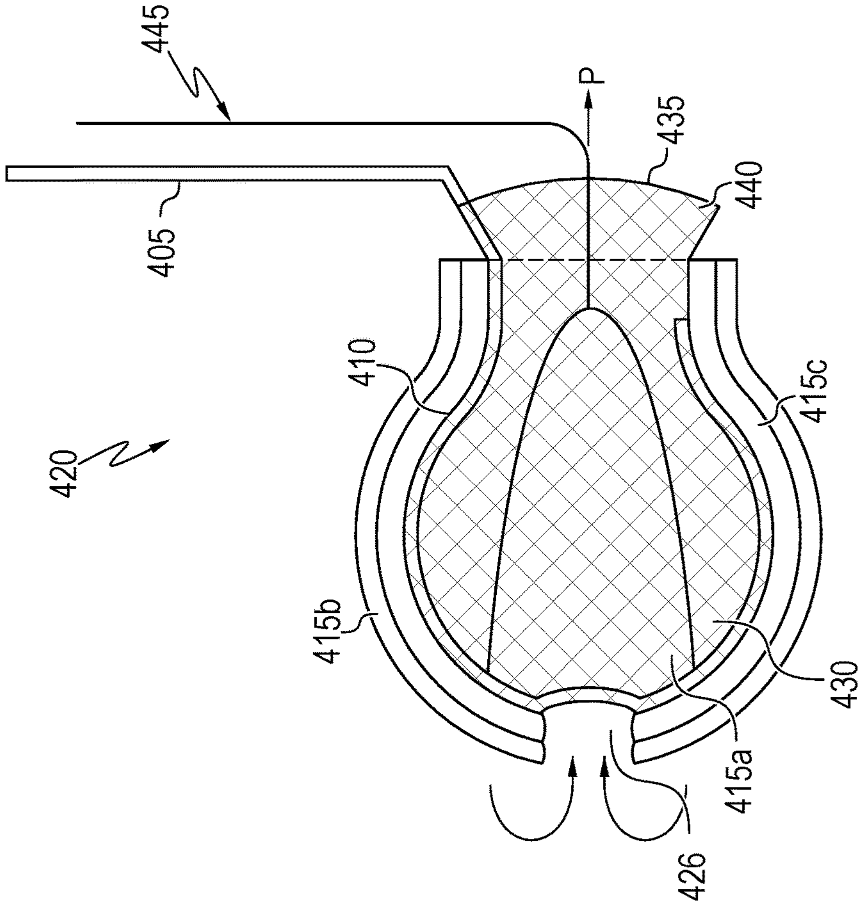
FIGS. 4A and 4B depict an alternative embodiment of an exemplary medical device in a first configuration (4A) and a second configuration (4B).
Figure 4A:
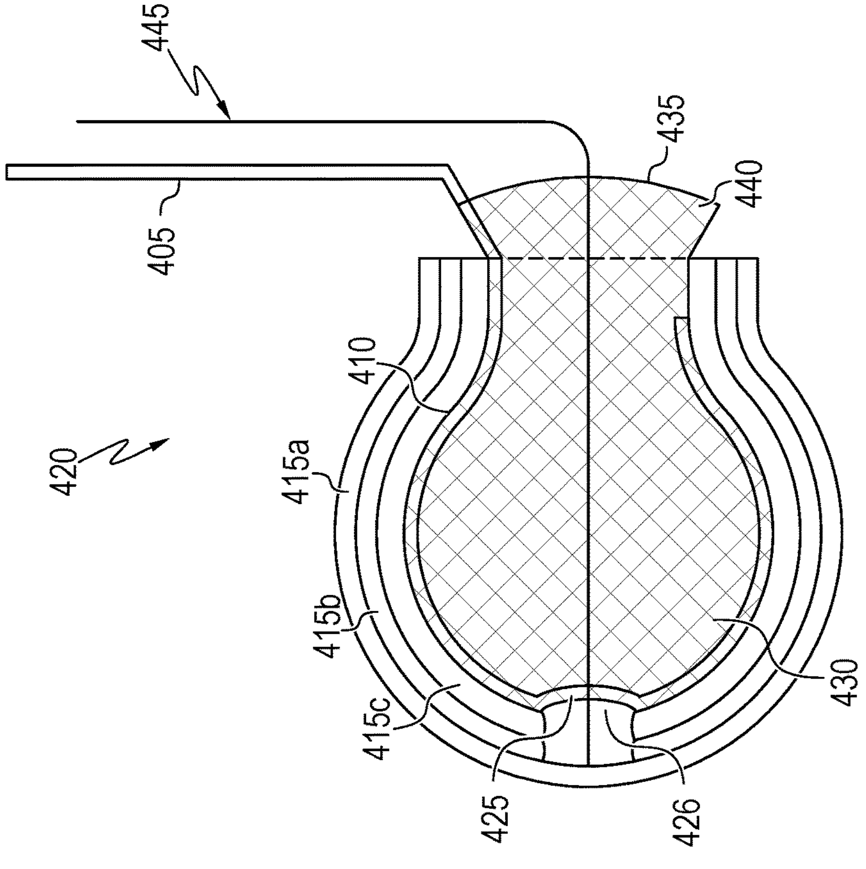

FIGS. 4A and 4B illustrate an alternative embodiment of a medical device 420. As in medical device 120, medical device 420 includes a negative pressure conduit 405 and an expanding frame 410 having a proximal end 435 and a distal end 425. Distal end 425 of expanding frame 410 may also comprise a terminal opening 426 wherein there is an absence of framing material. Similarly, expanding frame 410 may have a bulbous region 430 and a lip 440. These parts may have any of the structures and/or functions mentioned in connection with the same or similar parts of device 120.

Device 420 differs in that multiple discrete, separable sponge layers 415*a*, 415*b*, 415*c* lie over or surround expanding frame 410. In such a way, separable sponge layers 415*a*, 415*b*, 415*c* may be stacked. The number of sponge layers may be two, three, four, or any desired number. For example, multiple layers of sponge (e.g., 415*a*, 415*b*, 415*c*) may be utilized such that, during the course of treatment, the sponge material can be refreshed without redelivering or repositioning various devices. For example, once an outermost sponge layer 415*a* is used, the user may retract that sponge layer 415*a* using a pull line 445 (such as a line made of suture material or the like) or other means (i.e. forceps, snare, etc.) such that the outer sponge layer 415*a* is removed and a second layer 415*b* (previously beneath sponge layer 415*a*, and between sponge layer 415*a* and sponge layer 415*c*) is exposed. In such a way, separable sponge layers 415*a*, 415*b*, 415*c* may be individually removed. For example, sponge layer 415*a* may be removed without removing a remainder of medical device 420 (e.g., a distal portion of medical device 420) from the cavity. This may be accomplished by pulling sponge layer 415*a* through terminal opening 426 in a proximal direction (P), thereby revealing sponge layer 415*b*. Sponge layer 415*a* may then be extracted for analysis, if required.

Removing sponge layer 415*a* also may be accomplished by, for example, using a hot snare to cut off a section of sponge layer 415*a* for removal and/or analysis. Alternatively or additionally, the sponge layers 415*a*, 415*b*, etc. could include perforated sections or tear lines, which would enable the sponge layer(s) to tear away from the remaining sponge layer(s) once a predetermined force is exerted on the outermost sponge layer.

Additionally, for multiple sponge layers, multiple pull lines 445 may be used. For example, a second pull line (not shown) may be attached to sponge layer 415*b*, a third pull line (not shown) may be attached to sponge layer 415*c*, and so on. These pull lines may be color-coated or otherwise marked to indicate which pull line 445 corresponds to which sponge layer 415*a*, 415*b*, 415*c*, etc. For example, a green pull line may correspond to sponge layer 415*a*, a yellow pull line may correspond to sponge layer 415*b*, and a blue pull line may correspond to sponge layer 415*c*.

In some embodiments, each discrete sponge layer 415*a*, 415*b*, 415*c*, may differ from one another in one or more characteristics (e.g., coverage of the frame, pore size, dimension, material, color, etc.). For example, sponge layer 415*a* may be of one dimension, whereas sponge layer 415*b* and/or sponge layer 415*c* may be of another dimension, different from the first dimension. Similarly, sponge layer 415*a* may be of one material, whereas sponge layers 415*b*, 415*c* may be of another material, different from the first material. Additionally or alternatively, in some embodiments, each sponge layer 415*a*, 415*b*, etc. may be color coated or have different fluoroscopic markers to indicate the sponge layer 415*a*, 415*b* being used or removed. Various combinations of dimensions, materials, and colors are possible in such an embodiment.

Figure 5:
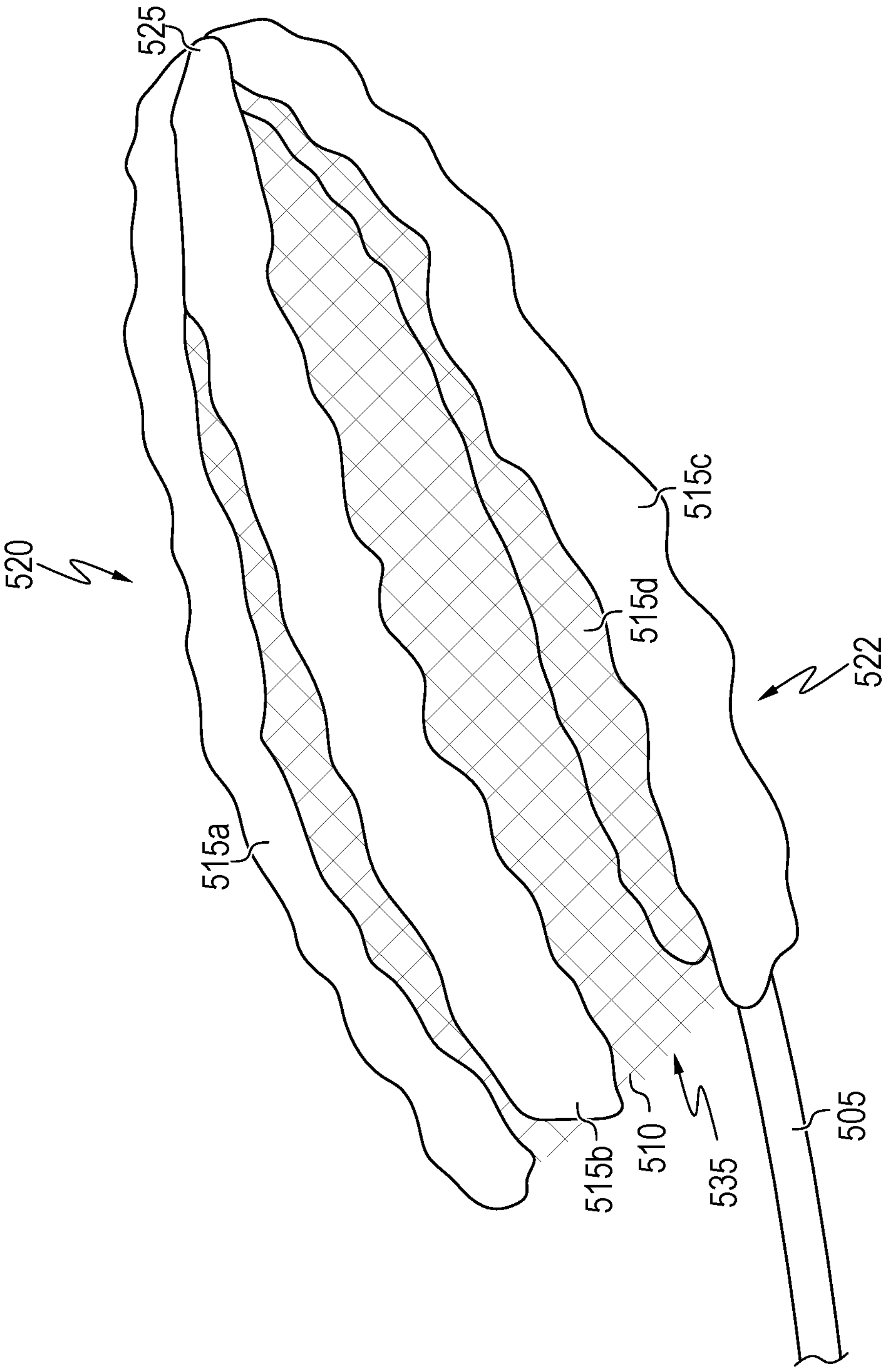
FIG. 5 is a perspective view of an alternative embodiment of an exemplary medical device, according to aspects of this disclosure.

FIG. 5 illustrates an alternative medical device 520 having an end effector 522. As in medical device 120, medical device 520 includes a negative pressure conduit 505 and an expanding frame 510 having a proximal end 535 and a distal end 525. These parts may have any of the structures and/or functions mentioned in connection with the same or similar parts of device 120. Medical device 520 differs in that strips 515*a*, 515*b*, 515*c*, 515*d* of sponge material extend longitudinally (proximally to distally) across expanding frame 510 from distal end 525 to proximal end 535 of expanding frame 510. Portions of the expanding frame 510 may be exposed in some embodiments. In other embodiments (not shown), expanding frame 510 may be completely covered by strips of sponge material.

Strips 515*a-d* meet at distalmost end 525. Strips 515*a-d* may overlap and/or be interleaved. Strips 515*a-d* allow for easy deployment and reconstrainment, if necessary due to the lesser volume of sponge than, for example, a solid conical sponge. Each strip 515*a*, 515*b*, 515*c*, 515*d* may be comprised of the same or different characteristics from one another. For example, the material, pore size, and/or dimensional characteristics for each strip may differ from one another. For example, strip 515*a* may be one material and one thickness and strip 515*b* may be a second material and/or a second thickness. Different thicknesses may also allow for easy removal of the device due to the lesser volume of sponge material as compared to a solid conical sponge. Similarly, the number of strips may differ in an alternative embodiment. For example, there may be one, two, three, four, or more strips of sponge. Moreover, the formation of the strips 515*a-d* is also not limited to extend longitudinally. For example, the strips of sponge may be spiraled (not shown) around expanding frame 510 or extend laterally around expanding frame 510, like rings. The strips of sponge may additionally or alternatively be layered, for example, combining aspects of the embodiment of FIGS. 4A-B with the present embodiment.

Figure 6:
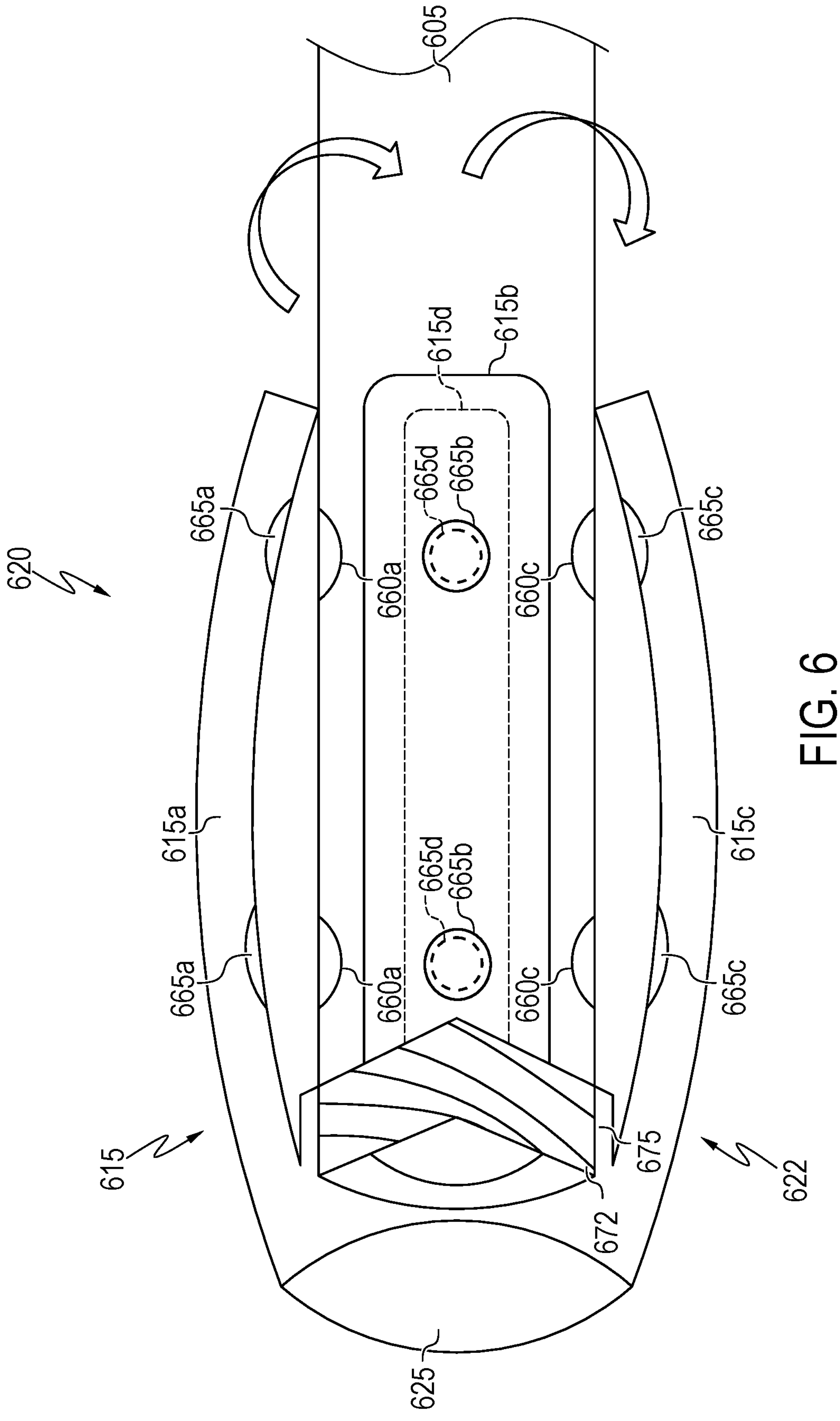
FIG. 6 is a perspective view of an alternative embodiment of an exemplary medical device, according to aspects of this disclosure.

FIG. 6 illustrates an alternative embodiment of a medical device 620 having an end effector 622. This embodiment of medical device 620 includes a suction conduit 605 that may have any of the characteristics of suction conduits described in other embodiments, except as described below. Medical device 620 further includes a sponge 615 having an arrangement of discrete strips 615*a*, 615*b*, 615*c*, 615*d*, etc. each extending axially in a proximal to distal direction. Discrete strips 615*a*-615*d* meet and connect at a distalmost end 625 of end effector 622. End effector 622 may include any number of strips 615*a*, 615*b*, 615*c*, etc., such as one, two, three, four, or more, evenly spaced or unevenly spaced about conduit 605. The embodiment shown in FIG. 6 includes four strips 615*a*-615*d* evenly spaced about conduit 605. Strips 615*a*, 615*c* are at the top and bottom of the page, respectively, and strips 615*b*, 615*d* are oriented out of and into the page respectively. Each strip 615*a*-615*d* faces radially inwards toward conduit 605. Each strip 615*a-d* may or may not include scaffolding (not shown) to help retain their shape, similar to the expandable frames described in previous embodiments.

Suction conduit 605 includes a screw fitting 675 corresponding to a screw fitting 672 on the inside distal wall of sponge 615. For example, conduit 605 may include a male or female screw fitting 675, and the inside distal wall of sponge 615 may include the corresponding female or male screw fitting 672. Alternative methods of attachment are also possible, so long as they permit relative rotational motion between sponge 615 and conduit 605. For example, a press-fitting or other method commonly known in the art may be utilized to movably couple sponge 615 with conduit 605.

Conduit 605 may include a plurality of pores 660*a*, 660*c* through the sidewall of conduit 605. Pores 660*a* may be spaced 180 degrees apart from pores 660*c*. Plurality of pores 660*a*, 660*c* align with a plurality of corresponding strategically placed suction sites 665*a*-665*d* on strips 615*a*-615*d*. Suction sites 665*a*-665*d* extend partially through a thickness of each corresponding strip 615*a*-615*c*. This embodiment may be configured such that, for example, in a first configuration, pores 660*a* and 660*c* align with pores or suction sites 665*a*, 665*c*, respectively, thereby influencing the application of suction to the surrounding tissue adjacent to or near the corresponding strips 615*a*, 615*c*. In a second configuration, wherein conduit 605 is torqued (e.g., rotated about an axis relative to sponge 615 by 90 degrees), suction pores 660*a*, 660*c* align with suction sites 665*d*. In the second configuration, the application of suction influences the surrounding tissue adjacent to or near corresponding strips 615*b*, 615*d*. Pores 660*a*, 660*c* may be offset such that, when pores 660*a*, 660*c* are aligned with secondary sites 665*a*, 665*c* (and their corresponding strips 615*a*, 615*c*), respectively, pores 660*a*, 660*c* are not aligned with secondary sites 665*b*, 665*d* (and their corresponding strips 615*b*, 615*d*), respectively, or vice versa.

Similar to previous embodiments, fluoroscopic markers, color coatings, or other markers can be utilized to help a user determine if the pores 660*a*, 660*c* and secondary sites 665*a*-665*d* are aligned appropriately. For example, one marker or color may show when pores 660*a*, 660*c* are aligned with sites 665*a*, 665*c* (and their strips 615*a*, 615*c*) in a first configuration, and a second marker or color different from the first marker or color may show when pores 660*a*, 660*c* are aligned with sites 665*b*, 665*d* (and their strips 615*b*, 615*d*).

Figure 7:
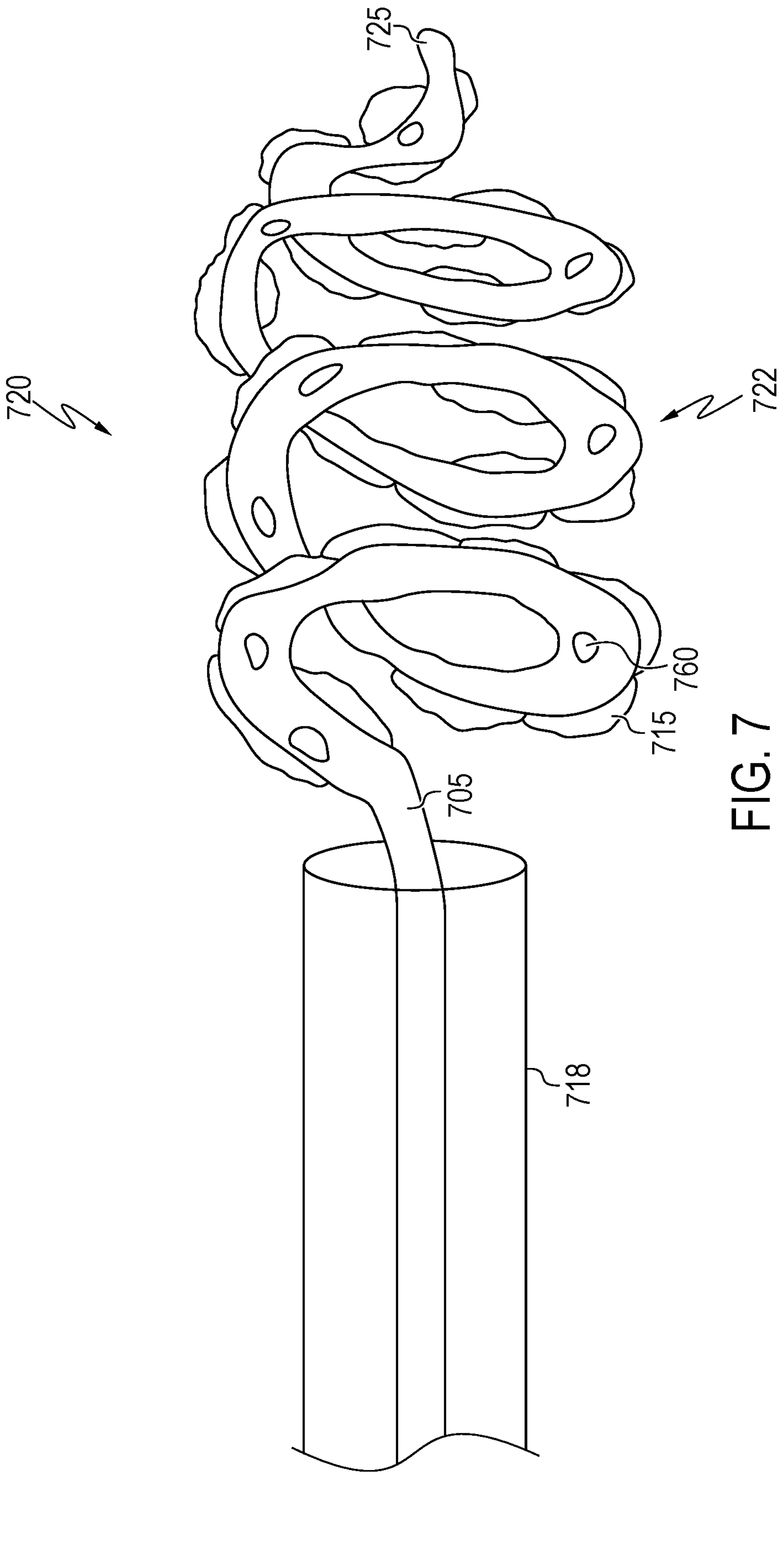
FIG. 7 is a side view of an alternative embodiment of an exemplary medical device, according to aspects of this disclosure.

FIG. 7 illustrates a side view of an exemplary medical device 720 including an end effector 722 comprising a suction conduit 705 and a porous body, e.g., sponge 715. Like other embodiments of medical devices described in this disclosure, medical device 720 may be flexible and configured to move through tortious pathways of the body lumens of a patient.

Suction conduit 705 may include a plurality of pores 760 through a wall of conduit 705. Pores 760 may be randomly or incrementally placed circumferentially around the suction conduit 705 for a specified distance so as to enable suction at a target site. A distalmost end of suction conduit 705 may comprise a rounded tip portion 725 configured to be atraumatic such that movement of end effector 722 within a body lumen of a patient does not cut or otherwise injure tissue. In alternative embodiments, suction conduit 705 may further comprise a central lumen (not shown) such that, when a coiled wire (not shown) is placed inside of the central lumen, a desired shape is imparted on the central lumen, and thereby imparted on the suction conduit 705. For example, the desired shape may be spherical, elliptical, pyramidal, cubical, or other shapes.

Sponge 715 may have any of the structures, characteristics, and/or functions mentioned in connection with the same or similar parts of device 120. For example, sponge 715 may be any suitable size and shape so as to fit within a patient's anatomy. Sponge 715 may comprise multiple pieces or one, large piece coupled to the space (e.g., outer surface/wall) of suction conduit 705. Sponge 715 may be removably coupled to suction conduit 705 by means of a central lumen (not shown) extending through sponge 715, wherein the central lumen may be sized to receive suction conduit 705, similar to a sock on a foot or a sleeve on an arm. In one embodiment, the sponge 715 may be coupled to suction conduit 705 by means of glue, a friction fit, or any alternative means commonly known in the art.

During use, medical device 720 is advanced through a sheath 718. End effector 722 of medical device 720, and particularly end effector 722, may be straight or substantially straight in a first configuration, wherein the sponge 715 and conduit 705 are inside of sheath 718. In a second, expanded configuration, end effector 722 may be coiled outside the delivery sheath 718 (e.g., when advanced distally to the delivery sheath 718). At least a portion of end effector 722 may take many shapes or forms in the second configuration, including spiraled, spherical, elliptical, pyramidal, cubical, and others. The expanded shape may be due to a natural bias to that expanded shape via, for example, shape memory materials used for at least the distal portion of conduit 705. Once end effector 722 is in a desired location, such as a cavity, perforation, or wound, a user may apply suction or negative pressure to device 720. Similar to the previous embodiments, suction is delivered for a desired amount of time. Once the procedure is complete, medical device 720 is removed from the patient, and a new medical device may be inserted, if desired.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and embodiments be considered as exemplary only.

The invention claimed is:

1. A medical device, comprising:

a tube having a sidewall defining a lumen within the tube, wherein a plurality of openings extend through a distal portion of the sidewall and are in fluid communication with the lumen, so that an application of suction within the lumen results in suction through the plurality of openings;

a support structure coupled to the distal portion of the sidewall, the support structure having a contracted configuration and an expanded configuration, and the support structure having support openings through a wall of the support structure, so that the suction through the plurality of openings results in suction through the support openings; and a porous body over at least a portion of the support structure, so that the suction through the support openings results in suction through pores of the porous body, wherein the porous body further comprises multiple stacked layers of porous material capable of being individually removed through a distal opening in the support structure and an interior of the support structure.

2. The medical device of claim 1, wherein the distal portion of the sidewall extends along an inside of the wall of the support structure.

3. The medical device of claim 1, wherein the plurality of openings are spaced along a distal length of the tube.

4. The medical device of claim 1, wherein the support structure further comprises an open proximal end through which the tube extends.

5. The medical device of claim 1, wherein the support structure, in the expanded configuration, comprises a distal bulbous region, a proximal region, and a lip region between the distal bulbous region and the proximal region, wherein a cross sectional dimension of the lip region is smaller than a cross sectional dimension of the distal bulbous region and a cross sectional dimension of the proximal region.

6. The medical device of claim 1, wherein the porous body is a flexible sponge.

7. The medical device of claim 1, wherein the porous body surrounds at least a portion of a circumference of the support structure.

8. The medical device of claim 1, wherein the porous body is affixed to the support structure.

9. The medical device of claim 1, wherein the porous body further comprises strips of material extending from a distal end to a proximal end of the support structure.

10. The medical device of claim 1, further comprising a tear line between adjacent stacked layers.

11. The medical device of claim 1, wherein at least one of the stacked layers is removable through the distal opening by pulling a pull line.

12. A medical device, comprising:

a sheath;

a tube having a sidewall defining a lumen within the tube, wherein a plurality of openings extend through a distal portion of the sidewall and are in fluid communication with the lumen, so that an application of suction within the lumen results in suction through the plurality of openings, wherein the tube includes a distal portion having a contracted configuration inside the sheath and an expanded configuration distal to the sheath; and a porous body over at least the distal portion of the tube, so that the suction through the plurality of openings results in suction through pores of the porous body, wherein the porous body further comprises multiple stacked layers of porous material capable of being individually removed through the lumen of the tube.

13. The medical device of claim 12, wherein the plurality of openings are spaced along the distal portion of the tube.

* * * * *